United States Patent [19]

Parsons

[11] 4,138,548
[45] Feb. 6, 1979

[54] ACARICIDAL PYRIDINIUM SALTS

[75] Inventor: John H. Parsons, Saffron Walden, England

[73] Assignee: Fisons Limited, England

[21] Appl. No.: 807,324

[22] Filed: Jun. 16, 1977

Related U.S. Application Data

[62] Division of Ser. No. 780,348, Mar. 23, 1977, which is a division of Ser. No. 545,700, Jan. 30, 1975, Pat. No. 4,025,632, which is a division of Ser. No. 321,476, Jan. 5, 1973, Pat. No. 3,886,171.

[30] Foreign Application Priority Data

Jan. 5, 1972 [GB] United Kingdom .................. 369/72

[51] Int. Cl.² .......................................... C07D 31/44
[52] U.S. Cl. ................... 542/421; 424/263; 424/266; 424/248.5; 424/248.54; 424/248.55; 424/248.51; 544/82
[58] Field of Search ..................... 542/421; 260/295 Q

[56] References Cited

U.S. PATENT DOCUMENTS

| | | | |
|---|---|---|---|
| 3,715,358 | 2/1973 | Witzel et al. | 424/263 |
| 3,838,159 | 9/1974 | Johnston | 424/263 |

OTHER PUBLICATIONS

Lown et al., Canadian J. Chem. 50 (1972), pp. 584–590.
Potts et al., J. Org. Chem. 33 (1968), pp. 3766–3770.

*Primary Examiner*—Arthur P. Demers
*Attorney, Agent, or Firm*—Wenderoth, Lind & Ponack

[57] ABSTRACT

A compound of the general formula

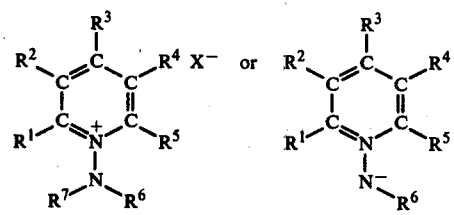

in which
$R^1$, $R^2$, $R^3$, $R^4$ and $R^5$ are the same or different and each represents hydrogen or alkyl of 1 to 4 carbon atoms;
$R^6$ represents a group of formula $COR^{10}$ in which $R^{10}$ represents styryl substituted by halogen;
$R^7$ represents hydrogen, alkyl of 1 to 4 carbon atoms or benzoyl substituted by halogen; and
$X^-$ represents one equivalent of an anion are acaricides, especially for use on crops.

6 Claims, No Drawings

ACARICIDAL PYRIDINIUM SALTS

This is a divisional application of application Ser. No. 780,348, filed Mar. 23, 1977, which is further a division of application Ser. No. 545,700, filed Jan. 30, 1975, now U.S. Pat. No. 4,025,632, which in turn is a division of application Ser. No. 321,476, filed Jan. 5, 1973, now U.S. Pat. No. 3,886,171.

This invention relates to acaricides.

A new group of acaricides has been discovered, which has very valuable properties. The compounds are of low mammalian toxicity. Moreover they are of low herbicidal and insecticidal activity and hence can be used to combat acarids on desired plants without harming the plants and to combat acarids without harming beneficial insects such as bees. Furthermore, besides having direct contact action against acarids, many of the compounds are systemic within plants and hence can be used on plants even though not all the affected parts of the plant are contacted during application and even by application to the soil in which the plants are growing or are to grow.

Accordingly, the invention includes a method of combating acarids at a locus infested or liable to be infested with them, which method comprises applying to the locus an acarid-combating amount of a compound of general formula

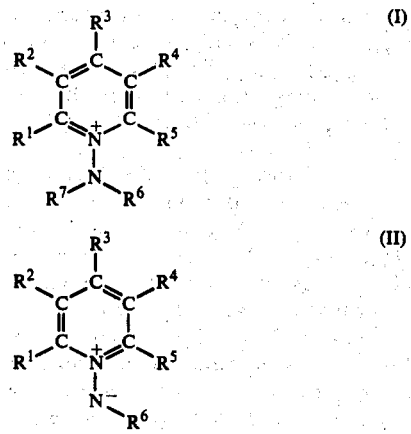

in which $R^1$, $R^2$, $R^3$, $R^4$ and $R^5$ are the same or different and each represents hydrogen, halogen (for example chloro or bromo), nitro, alkyl (for example of 1 to 4 carbon atoms such as methyl, ethyl or isopropyl), substituted alkyl (for example the alkyl group substituted by hydroxy or halogen, such as hydroxymethyl, chloromethyl or trifluoromethyl), alkoxy (for example of 1 to 4 carbon atoms such as methoxy, ethoxy or isopropoxy), carboxy or an ester (for example with an alkanol of 1 to 4 carbon atoms), amide or mono- or di-substituted amide (for example substituted by alkyl of 1 to 4 carbon atoms) thereof, aryl (for example phenyl), heterocyclic (for example furyl, morpholino or a second group of formula I or II in which one of $R^1$, $R^2$, $R^3$, $R^4$ and $R^5$ is merely a bond), aralkyl (for example whose alkyl group contains 1 to 4 carbon atoms, such as benzyl or phenethyl), cyano or hydroxy; $R^6$ represents a group of formula $COR^8$, $CO.OR^8$, $CONR^8R^9$ or $SO_2R^8$ in which $R^8$ represents alkyl (for example of 1 to 8 preferably 1 to 4 carbon atoms such as methyl, ethyl or isopropyl), substituted alkyl (for example the alkyl group substituted by halogen, alkoxycarbonyl of 2 to 5 carbon atoms, alkoxy, e.g. of 1 to 4 carbon atoms, or by phenoxy substituted by halogen and/or alkyl of 1 to 4 carbon atoms, such as trifluoromethyl, chloroethyl, ethoxyethyl or 2-methyl-4-chlorophenoxymethyl), aryl (for example phenyl), substituted aryl (for example the aryl group substituted by one or more groups selected from halogen, alkyl of 1 to 4 carbon atoms, acetamido, nitro and alkoxy of 1 to 4 carbon atoms, such as chlorophenyl, dichlorophenyl, tolyl, xylyl, fluorophenyl, nitrophenyl, methoxyphenyl or 3-methyl-4-chlorophenyl), aralkyl (for example whose alkyl group contains 1 to 4 carbon atoms, such as benzyl), substituted aralkyl (for example the aralkyl group substituted by halogen, such as chlorobenzyl), aralkenyl (for example styryl), substituted aralkenyl (for example the aralkenyl group substituted by halogen, such as chlorostyryl), cycloalkyl (for example of 3 to 8 carbon atoms, such as cyclohexyl) or heterocyclic (for example furyl, thienyl, benzofuryl or pyridyl), and $R^9$ represents hydrogen, alkyl (for example of 1 to 8 preferably 1 to 4 carbon atoms such as methyl, ethyl or isopropyl), substituted alkyl (for example the alkyl group substituted by halogen or alkoxy, e.g. of 1 to 4 carbon atoms, such as trifluoromethyl, chloroethyl or ethoxyethyl), phenyl or substituted phenyl (for example substituted by halogen or alkyl of 1 to 4 carbon atoms, such as chlorophenyl, dichlorophenyl, tolyl or xylyl); $R^7$ represents hydrogen, alkyl of 1 to 4 carbon atoms or a group as defined under $R^6$; and $X^-$ represents one equivalent of an anion (for example $Cl^-$, $Br^-$, $I^-$, $CH_3SO_4^-$, $NO_3^-$ or $\frac{1}{2} SO_4^{2-}$); with the proviso that $R^3$ is not a second group of formula I or II in which $R^3$ is merely a bond. The substituents defined above include acidic and basic groups and where salt formation can take place as a result at such groups, the compounds may be present as such salts. For example 1-nicotinamido-3-methylpyridinium chloride may be in the form of its hydrochloride, 1-nicotinamido-3-methylpyridinium chloride hydrochloride.

In addition, the invention includes as new compounds the present compounds except those in which $R^6$ represents acetyl, propionyl, trifluoroacetyl, benzoyl, methoxycarbonyl, ethoxycarbonyl, p-tolylsulphonyl, sulphanilyl or N-acetylsulphanilyl.

The invention also provides acaricidal compositions containing the present compounds, particularly a composition comprising such a compound together with a surface active agent; a solid composition comprising such a compound together with a solid carrier; a liquid composition comprising such a compound together with a hydrocarbon of boiling point in the range 130°–270° C.; and a composition comprising such a compound together with another agrochemical pesticide especially another acaricide.

The compounds of formula I may be prepared by reacting a 1-amino-pyridinium salt of formula

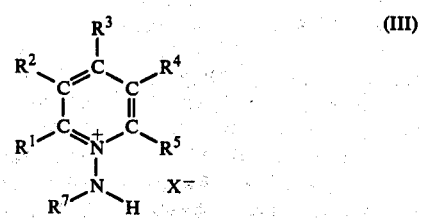

with a halide or anhydride of formula $R^6Y$ or $R^6OR^6$ respectively (in which Y represents halogen). The reaction may be carried out in an organic solvent in which the desired product is insoluble, for example a hydrocarbon such as xylene. Alternatively the reaction may be carried out without a solvent, using excess of the compound $R^6Y$ or $R^6OR^6$.

Alternatively, compounds of formula I may be prepared by reacting a compound of formula II with a compound of formula $R^7X$. When $R^7$ represents hydrogen, an external salt of formula I corresponding to the internal salt of formula II is simply prepared; but when $R^7$ represents other than hydrogen (e.g. when the compound of formula $R^7X$ is dimethyl sulphate or p-chlorobenzoyl chloride), an external salt of formula I which has no counterpart of formula II is prepared.

The compounds of formula II may be prepared by treating those of formula I wherein $R^7$ represents hydrogen with a base, such as sodium hydroxide.

It can be seen that the compounds of formula II are the corresponding internal salts of the compounds of formula I wherein $R^7$ represents hydrogen. Such compounds of the two types are equivalent. In aqueous solution of such compounds of formula I an equilibrium exists with the compounds of formula II, for example:

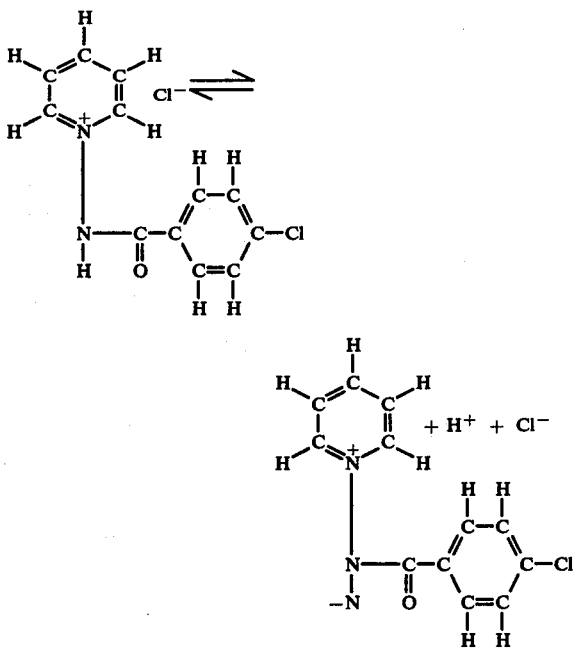

Such pairs of equivalent compounds are of similar activity in use. Since in the compounds of formula I it is the cation which is responsible for the acaricidal activity, any anion can generally be employed and it can thus be chosen bearing other factors in mind such as convenience in manufacture of the cation. $X^-$ is suitably chloride.

In a particular embodiment of the present compounds $R^1$, $R^2$, $R^3$, $R^4$ and $R^5$ are the same or different and each represents hydrogen, halogen, nitro, alkyl, substituted alkyl, alkoxy, carboxy or an ester, amide or mono- or di-substituted amide thereof, aryl, aralkyl, cyano or hydroxy. New compounds within this group include the compounds in which $R^6$ represents $CONR^8R^9$; $COR^{10}$ in which $R^{10}$ represents substituted aryl, aralkyl, substituted aralkyl, aralkenyl, substituted aralkenyl, cycloalkyl or heterocyclic; $COOR^{11}$ in which $R^{11}$ represents substituted alkyl, aryl, substituted aryl, aralkyl, substituted aralkyl, aralkenyl, substituted aralkenyl, cycloalkyl or heterocyclic; or $SO_2R^{12}$ in which $R^{12}$ represents alkyl, substituted alkyl, aryl, aralkyl, substituted aralkyl, aralkenyl, substituted aralkenyl, cycloalkyl or heterocyclic.

In another particular embodiment, $R^1$, $R^2$, $R^3$, $R^4$ and $R^5$ are the same or different and each represents hydrogen, halogen, nitro, alkyl, alkoxy, carboxy or an ester, amide or mono- or di-substituted amide thereof, aryl, aralkyl or hydroxy; $R^8$ represents alkyl, substituted alkyl, phenyl or substituted phenyl; and $R^7$ represents hydrogen. Preferred amongst this group of compounds are those wherein $R^8$ is phenyl optionally substituted, preferably monosubstituted, by chlorine. New compounds within the group include the compounds in which $R^6$ represents $CONR^8R^9$; $COR^{10}$ in which $R^{10}$ represents substituted phenyl; $COOR^{11}$ in which $R^{11}$ represents substituted alkyl, phenyl or substituted phenyl; or $SO_2R^{12}$ in which $R^{12}$ represents alkyl, substituted alkyl or phenyl.

A more specific group of the present compound are those wherein $R^1$, $R^2$, $R^3$, $R^4$ and $R^5$ are the same or different and each represents hydrogen, halogen, nitro, alkyl of 1 to 4 carbon atoms, alkyl of 1 to 4 carbon atoms substituted by hydroxy or halogen, alkoxy of 1 to 4 carbon atoms, carboxy, alkoxycarbonyl whose alkoxy group contains 1 to 4 carbon atoms, carbamoyl, N-alkylcarbamoyl whose alkyl group contains 1 to 4 carbon atoms, N,N-dialkylcarbamoyl whose alkyl groups are the same or different and contain 1 to 4 carbon atoms, phenyl, furyl, morpholino, a second group of formula I or II in which one of $R^1$, $R^2$, $R^3$, $R^4$ and $R^5$ is merely a bond, phenylalkyl of 7 to 10 carbon atoms, cyano or hydroxy, with the proviso that $R^3$ does not represent a second group of formula I or II in which $R^3$ is merely a bond; $R^8$ represents alkyl of 1 to 8 carbon atoms; alkyl of 1 to 8 carbon atoms substituted by halogen, alkoxycarbonyl of 2 to 5 carbon atoms, alkoxy of 1 to 4 carbon atoms, or by phenoxy substituted by halogen and/or alkyl of 1 to 4 carbon atoms; phenyl; naphthyl; phenyl or naphthyl substituted by one or more groups selected from halogen, alkyl of 1 to 4 carbon atoms, nitro and alkoxy of 1 to 4 carbon atoms; phenylalkyl of 7 to 10 carbon atoms, substituted by halogen; styryl; styryl substituted by halogen; cycloalkyl of 3 to 8 carbon atoms; furyl; thienyl; benzofuryl; or pyridyl; and $R^9$ represents hydrogen; alkyl of 1 to 8 carbon atoms; alkyl of 1 to 8 carbon atoms substituted by halogen or alkoxy of 1 to 4 carbon atoms; phenyl; or phenyl substituted by halogen or alkyl of 1 to 4 carbon atoms.

For convenience in manufacture, the present compounds can be those wherein $R^1$, $R^2$, $R^3$, $R^4$ and $R^5$ are the same or different and each represents hydrogen or alkyl of 1 to 4 carbon atoms; $R^8$ represents alkyl of 1 to 8 carbon atoms; alkyl of 1 to 8 carbon atoms substituted by alkoxycarbonyl of 2 to 5 carbon atoms or by phenoxy substituted by halogen and/or alkyl of 1 to 4 carbon atoms; phenyl; naphthyl; phenyl substituted by one or more groups selected from halogen, alkyl of 1 to 4 carbon atoms, nitro and alkoxy of 1 to 4 carbon atoms; phenylalkyl of 7 to 10 carbon atoms; phenylalkyl of 7 to 10 carbon atoms substituted by halogen; styryl; styryl substituted by halogen; cycloalkyl of 3 to 8 carbon atoms; furyl; thienyl; benzofuryl; or pyridyl; $R^9$ represents hydrogen or alkyl of 1 to 8 carbon atoms; and $R^7$ represents hydrogen, alkyl of 1 to 4 carbon atoms or benzoyl substituted by halogen. A preferred group of these compounds are those wherein $R^8$ represents alkyl of 1 to 8 carbon atoms; alkyl of 1 to 8 carbon atoms substituted by phenoxy substituted by halogen; phenyl; phenyl substituted by one or more groups selected from halogen, alkyl of 1 to 4 carbon atoms, nitro and alkoxy of 1 to 4 carbon atoms; phenylalkyl of 7 to 10 carbon atoms; styryl; styryl substituted by halogen; cycloalkyl of 3 to 8 carbon atoms; benzofuryl; or pyridyl.

It is preferred that $R^7$ represents hydrogen.

Usually at least three, and preferably at least four, of $R^1$, $R^2$, $R^3$, $R^4$ and $R^5$ represent hydrogen.

Preferably at least one of $R^1$ and $R^5$ represents hydrogen.

The most preferred compounds are those wherein $R^6$ represents $COR^8$ or $COOR^8$ especially where $R^8$ represents phenyl substituted by one or more groups selected from halogen, alkyl of 1 to 4 carbon atoms, nitro and alkoxy of 1 to 4 carbon atoms. Such especially preferred compounds are not only highly active but are active over long periods, e.g. 1-(p-chlorobenzamido)-pyridinium chloride can protect cucumbers for 2 months or more. Moreover, such especially preferred compounds are active against strains of mites which are resistant to standard acaricides, such as Dicofol, Chlorobenzilate, Tetradifon and Dimethoate.

A preferred group of new compounds are those of general formula I or II in which $R^1$, $R^2$, $R^3$, $R^4$ and $R^5$ are the same or different and each represents hydrogen or alkyl of 1 to 4 carbon atoms; $R^6$ represents a group of formula $COR^{10}$, $COOR^{11}$, or $CONR^{13}R^{14}$ in which $R^{10}$ represents phenyl substituted by one or more groups selected from halogen, alkyl of 1 to 4 carbon atoms, nitro and alkoxy of 1 to 4 carbon atoms; phenylalkyl of 7 to 10 carbon atoms; phenylalkyl of 7 to 10 carbon atoms substituted by halogen; styryl; styryl substituted by halogen; cycloalkyl of 3 to 8 carbon atoms; furyl; pyridyl; benzofuryl or thienyl; $R^{11}$ represents phenyl; phenyl substituted by halogen and/or alkyl of 1 to 4 carbon atoms; or benzofuryl; $R^{13}$ represents alkyl of 1 to 8 carbon atoms; phenyl; phenyl substituted by one or more groups selected from halogen, alkyl of 1 to 4 carbon atoms and alkoxy of 1 to 4 carbon atoms; and $R^{14}$ represents hydrogen or alkyl of 1 to 8 carbon atoms; $R^7$ represents hydrogen, alkyl of 1 to 4 carbon atoms or benzoyl substituted by halogen; and $X^-$ represents one equivalent of an anion. Desirably within this group $R^{10}$ represents phenyl substituted by one or more groups selected from halogen, alkyl of 1 to 4 carbon atoms, nitro and alkoxy of 1 to 4 carbon atoms; phenylalkyl of 7 to 10 carbon atoms; styryl; styryl substituted by halogen; cycloalkyl of 3 to 8 carbon atoms; or pyridyl; $R^{11}$ represents phenyl; phenyl substituted by halogen and/or alkyl of 1 to 4 carbon atoms; or benzofuryl; and $R^{13}$ represents alkyl of 1 to 8 carbon atoms or phenyl substituted by halogen.

Outstandingly active and most preferred are compounds of general formula I and II in which four of $R^1$, $R^2$, $R^3$, $R^4$ and $R^5$ represent hydrogen and the fifth represents hydrogen or alkyl of 1 to 4 carbon atoms; $R^6$ represents benzoyl substituted by one or two substituents selected from halogen, alkyl of 1 to 4 carbon atoms and nitro; and $X^-$ represents one equivalent of an anion. The most promising particular compounds within this group are:

1-(p-chlorobenzamido)pyridinium salts;
1-(p-chlorobenzamido)-2-methylpyridinium salts;
1-(p-chlorobenzamido)-3-methylpyridinium salts;
1-(p-chlorobenzamido)-4-methylpyridinium salts;
1-(3,4-dichlorobenzamido)pyridinium salts; and
1-(4-nitrobenzamido)pyridinium salts;
especially the first-mentioned and especially the internal salts of these compounds and the chlorides of the first five.

The present compounds are usually employed in the form of compositions containing the active ingredients. Usually compositions are initially produced in the form of concentrates, e.g. containing 20–98% active ingredient, and these are diluted with water for application, e.g. so that the concentration of active ingredient is 0.01–0.5%. Parts and percentages in this specification are by weight unless otherwise indicated.

The compositions normally contain a carrier and/or a surface active agent.

The carrier may be a liquid, e.g. water (e.g. water used to dilute a concentrate for application). Many of the compounds are water soluble crystalline solids and can be used in the form of aqueous solutions. If water is employed as carrier in a concentrate, an organic solvent may also be present as carrier, though this is not usually employed. A surface active agent may advantageously be present.

The carrier may be a liquid other than water, for example an organic solvent usually a water-immiscible solvent, e.g. a hydrocarbon which boils within the range 130°–270° C., in which the compounds are dissolved or suspended. A concentrate containing an organic solvent suitably also contains a surface active agent so that the concentrate acts as a self-emulsifiable oil on admixture with water.

The carrier may be a solid, which may be finely divided. Examples of suitable solids are clays, sand, mica, chalk, attapulgite, diatomite, perlite and sepiolite, and synthetic solid carriers, e.g. silicas, silicates and ligno-sulphonates.

Wettable powders soluble or dispersible in water may be formed by admixing the compounds with or without a carrier with a surface active agent.

Aqueous solutions and wettable powders are the preferred concentrates since the compounds are of comparatively low solubility in organic solvents such as hydrocarbons. A compound of formula I where $R^7$ represents hydrogen tends to be more soluble in water but less soluble in organic solvents such as hydrocarbons than the corresponding compound of formula II. Thus, in making up an emulsifiable concentrate in a hydrocarbon the compound in the form of an internal salt of formula II would generally be favoured, while in making up an aqueous solution the compound in the form of an external salt of formula I would generally be favoured.

The term 'surface active agent' is used in the broad sense to include materials variously called emulsifying agents, dispersing agents and wetting agents. Such agents are well known in the art.

The surface active agents used may comprise anionic surface active agents, for example soaps, fatty sulphate esters such as dodecyl sodium sulphate, octadecyl sodium sulphate and cetyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic agents, for example condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers or ethylene oxide and propylene oxide.

The surface active agents may also comprise cationic agents, for example cetyl trimethylammonium bromide.

Preferred surface active agents are non-ionic surface active agents.

The present compounds are useful as acaricides. They are particularly active against the eggs of mites, preventing the eggs from hatching, and are also active against the larval and nymphal stages. Furthermore, when adult female mites are treated with a non-toxic dosage of the compounds, the mites' eggs fail to hatch.

The present active compounds may be admixed with other agrochemical pesticides, for example herbicides, insecticides, fungicides or other acaricides, or fertilizers. Examples of pesticides with which the compounds may be mixed are Dicofol (2,2,2-trichloro-1,1,-di(4-chlorophenyl)ethanol), Fenazaflor (5,6-dichloro-1-phenoxycarbonyl-2-trifluoromethylbenzimidazole), tricyclohexyltin hydroxide, Tetradifon (2,4,4',5-tetrachlorodiphenyl sulphone), Formetanate (3-dimethylaminomethyleneiminophenyl N-methylcarbamate), Chlorodimeform (N,N-dimethyl-N'-(2-methyl-4-chlorophenyl)formamidine), Chlorobenzilate (ethyl 4,4'-dichlorobenzilate), Quinomethionate (6-methyl-2-oxo-1,3-dithiolo[4,5-b]quinoxaline), Endosulfan (6,7,8,9,10,10-hexachloro-1,5,5a,6,9,9a-hexahydro-6,9-methano-2,4,3-benzodioxathiepin 3-oxide), Chlorodecone (decachlorooctahydro-1,3,4-metheno-2H,5H,cyclobuta[cd]pentalen-2-one), bis(pentachloro-2,4-cyclopentadien-1-yl), Chloropropylate (isopropyl 4,4'-dichlorobenzilate), Bromopropylate (isopropyl 4,4'-dibromobenzilate), Thioquinox (2-thio-1,3-dithiolo-[4,5-b]quinoxaline), Dinocap (dinitrooctylphenyl crotonate), Binapacryl (2-sec-butyl-4,6-dinitrophenyl 2-methylcrotonate), Dinobuton (2-sec-butyl-4,6-dinitrophenyl isopropyl carbonate), Naled (1,2-dibromo-2,2-dichloroethyl dimethyl phosphate), Monocrotophos (dimethyl 1-methyl-2-(methylcarbamoyl)-vinyl phosphate), Demeton (diethyl 2-(ethylthio) ethylthiophosphate), Phorate (O,O-diethyl S-(ethylthiomethyl) phosphorodithioate), Oxydemeton-methyl (O,O-dimethyl S-(2,ethylsulphinylethyl)phosphorothioate), Ethion (tetraethyl S,S'-methylenebis(phosphorodithioate)), Formothion (S-(N-formyl-N-methylcarbamoylmethyl) dimethyl phosphorodithioate), Ethoate-methyl (S-(N-ethylcarbamoylmethyl) dimethyl phosphorodithioate), Dimethoate (dimethyl S-(N-methylcarbonylmethyl) phosphorodithioate), Cyanthoate (S-(N-(1-cyano-1-methylethyl)carbamoylmethyl) diethyl phosphorothioate), EPN (O-ethyl O-p-nitrophenyl phenylphosphonothioate), Carbophenothion (S-(4-chlorophenylthiomethyl) diethyl phosphorodithioate), Methidathion (S-(2,3-dihydro-5-methoxy-2-oxo-1,3,4-thiadiazol-3-ylmethyl) dimethyl phosphorodithioate), Clorpyrifos (diethyl 3,5,6-trichloro-2-pyridyl phosphorothionate), Diazinon (diethyl 2-isopropyl-6-methyl-4-pyrimidinyl phosphorothionate), Azinphos-ethyl (diethyl S-(4-oxo-1,2,3-benzotriazin-3-ylmethyl) phosphorodithioate), Azinphos-methyl (dimethyl S-(4-oxo-1,2,3-benzotriazin-3-ylmethyl phosphorodithioate), Fenson (4-chlorophenyl benzenesulphonate), Tetrasul (2,4,4',5-tetrachlorodiphenyl sulphide), Chlorbenside (4-chlorobenzyl 4-chlorophenyl sulphide), Chlorfensulphide (4-chlorophenyl 2,4,5-trichlorophenylazo sulphide) 2-(p-tert-butylphenoxy)-1-methylethyl 2chloroethyl sulphite, 2-(p-tert-butylphenoxy)cyclohexyl 2-propynyl sulphite, Aldicarb (2-methyl-2-(methylthio)propionaldehyde O-(methylcarbamoyl)oxime), Methomyl (S-methyl-N-(Methylcarbamoyloxy) thioacetimidate), Methiocarb (4-methylthio-3,5-xylyl N-methylcarbamate), and Benomyl (methyl 1-(butylcarbamoyl)benzimidazole-2-carbamate).

Particularly useful are mixtures with other acaricides which have rapid knockdown to adult mites. These mixtures combine activity against adult mites and ovicidal activity against the following generation. A particularly suitable such acaricide is Dicofol.

Mixtures with insecticides are useful in broadening the spectrum of pest species against which the compositions are effective.

Mixtures with fungicides can combine protection against mites with protection against fungi. Particularly useful are mixtures with fungicides controlling scab and mildew diseases, such as Benomyl, Dinocap and Quinomethionate.

The present compositions may be formed by admixing the ingredients.

The compounds may be applied to stored products, animals, the land, the soil or plants. The compounds are of interest particularly to combat mites which infest or are liable to infest desired plants especially crops and particularly food crops. Preferably, the compounds are applied to crops or to soil in which crops are growing or are immediately after application to grow. The compounds are safe to a wide variety of crops and can be used against mites in the field or in the greenhouse. Examples of crops on which the compounds can be used are apples, pears, strawberries, plums, citrus, vines, cotton, ornamentals, cucumbers and tomatoes. When applied to land, the soil or plants, the compounds may generally be used at a rate within the range 0.1–4, preferably 0.1–2, kg per hectare. They are active against various mite species for example the greenhouse red spider mite, *Tetranychus telarius* and hop red spider mite *Tetranchus urticae.*

The invention is illustrated by the following Examples.

EXAMPLE 1

1-Aminopyridinium chloride (104 parts) and p-chlorobenzoyl chloride (150 parts) were heated in xylene (750 parts) at 140° C. for 4 hours. The solid product was filtered off and recrystallised from n-butanol to give 1-(p-chlorobenzamido)pyridinium chloride (209 parts, 97% yield), melting point 241° C.

Analysis: Found: C, 53.60; H, 3.85; N, 10.60%. $C_{12}H_{10}Cl_2N_2O$ requires: C, 53.55; H, 3.75; N, 10.41%.

EXAMPLE 2

1-Aminopyridinium chloride (20 parts) and n-butyric anhydride (100 parts) were heated at 100° C. for 4 hours. On cooling, a crystalline solid formed which was filtered off and washed with ethyl acetate to give 1-butyramidopyridinium chloride (19 parts, 62% yield), melting point 125° C.

Analysis: Found: C, 53.70; H, 6.30; N, 14.15%. $C_9H_{13}ClN_2O$ requires: C, 53.87; H, 6.53; N, 13.96%.

EXAMPLES 3–95

The following were prepared by analogous methods to those of Examples 1 and 2:

| | |
|---|---|
| 1-Acetamidopyridinium chloride | m.p. 222° C. |
| 1-(Ethoxycarbonylamino)pyridinium chloride | m.p. 160° C. |
| 1-Nonanamidopyridinium chloride | m.p. 139° C. |
| 1-Benzamidopyridinium chloride | m.p. 233° C. |
| 1-(p-Fluorobenzamido)pyridinium chloride | m.p. 230° C. |
| 1-(p-Toluamido)pyridinium chloride | m.p. 245° C. |
| 1-(2,4-Dichlorobenzamido)pyridinium chloride | m.p. 242° C. |
| 1-(p-Nitrobenzamido)pyridinium chloride | m.p. 240° C. |
| 1-(m-Nitrobenzamido)pyridinium chloride | m.p. 200° C. |
| 1-(p-Chlorobenzamido)-2-methylpyridinium chloride | m.p. 195° C. |
| 1-(p-toluamido)-2-methylpyridinium chloride | m.p. 248° C. |
| 1-(3,4-dichlorobenzamido)pyridinium chloride | m.p. 218° C. |
| 1-benzamido-2-methylpyridinium chloride | m.p. 208° C. |
| 1-(3,4-dichlorobenzamido)-2-methylpyridinium chloride | m.p. 220° C. |
| 1-(o-chlorobenzamido)pyridinium chloride | m.p. 203° C. |
| 1-(p-anisamido)pyridinium chloride | m.p. 219° C. |
| 1-(p-nitrobenzamido)-2-methylpyridinium chloride | m.p. 200° C. |
| 1-(o-iodobenzamido)pyridinium chloride | m.p. 230° C. |
| 1-(p-chlorobenzamido)-4-methylpyridinium chloride | m.p. 248° C. |
| 1-(o-toluamido)pyridinium chloride | m.p. 203° C. |
| 1-(o-toluamido)-4-methylpyridinium chloride | m.p. 205-8° C. |
| 1-(p-tert-butylbenzamido)pyridinium chloride | m.p. 234-6° C. |
| 1-(p-tert-butylbenzamido)-4-methylpyridinium chloride | m.p. 222-5° C. |
| 1-(o-chlorobenzamido)-2-methylpyridinium chloride | m.p. 220° C. |
| 1-(m-chlorobenzamido)pyridinium chloride | m.p. 230° C. |
| 1-(m-chlorobenzamido)-2-methylpyridinium chloride | m.p. 203° C. |
| 1-(m-chlorobenzamido)-3-methylpyridinium chloride | m.p. 195° C. |
| 1-(m-chlorobenzamido)-4-methylpyridinium chloride | m.p. 228° C. |
| 1-(p-chlorobenzamido)-3-methylpyridinium chloride | m.p. 214-6° C. |
| 1-(p-chlorobenzamido)-2-ethylpyridinium chloride | m.p. 191-3° C. |
| 1-(p-chlorobenzamido)-2,4-dimethylpyridinium chloride | m.p. 224° C. |
| 1-(p-chlorobenzamido)-3,5-dimethylpyridinium chloride | m.p. 222-6° C. |
| 1-(p-chlorobenzamido)-2,6-dimethylpyridinium chloride | m.p. 235-40° C. |
| 1-(p-chlorobenzamido)-5-ethyl-2-methylpyridinium chloride | m.p. 188-190° C. |
| 1-(p-bromobenzamido)pyridinium chloride | m.p. 244-50° C. |
| 1-(p-iodobenzamido)pyridinium chloride | m.p. 260-3° C. |
| 1-(m-anisamido)pyridinium chloride | m.p. 246-8° C. |
| 1-(m-anisamido)-4-methylpyridinium chloride | m.p. 205-8° C. |
| 1-(3,4-dimethylbenzamido)pyridinium chloride | m.p.210° C. |
| 1-(3,4-dimethylbenzamido)-3-methylpyridinium chloride | m.p. 240-3° C. |
| 1-(3,4-dichlorobenzamido)-2,6-dimethylpyridinium chloride | m.p. 245-55° C. |
| 1-(3-chloro-p-toluamido)pyridinium chloride | m.p. 224-5° C. |
| 1-(3-chloro-p-toluamido)-2-methylpyridinium chloride | m.p. 233-5° C. |
| 1-(3-chloro-p-toluamido)-4-methylpyridinium chloride | m.p. 232-4° C. |
| 1-(4-chloro-m-toluamido)pyridinium chloride | m.p. 223-4° C. |
| 1-(4-chloro-m-toluamido)-2-methylpyridinium chloride | m.p. 189-191° C. |
| 1-(4-chloro-m-toluamido)-4-methylpyridinium chloride | m.p. 194-196° C. |
| 1-(3,6-dichloro-o-anisamido)pyridinium chloride | m.p. 205-7° C. |
| 1-(4-nitro-m-toluamido)pyridinium chloride | m.p. 242-6° C. |
| 1-(4-nitro-m-toluamido)-3-methylpyridinium chloride | m.p. 240-4° C. |
| 1-(4-chloro-3-nitrobenzamido)-3-methylpyridinium chloride | m.p. 220-2° C. |
| 1-(3-(methoxycarbonyl)propionamido)pyridinium chloride | m.p. 165° C. |
| 1-(cyclohexylcarboxamido)pyridinium chloride | m.p. 185° C. |
| 1-(1-naphthamido)pyridinium chloride | m.p. 253-5° C. |
| 1-(2-naphthamido)pyridinium chloride | m.p. 234-6° C. |
| 1-(2-furamido)pyridinium chloride | m.p. 214-8° C. |
| 1-nicotinamido-3-methylpyridinium chloride, hydrochloride | m.p. 205-212° C. |
| 1-nicotinamido-4-methylpyridinium chloride, hydrochloride | m.p. 250-3° C. |
| 1-(2-phenylacetamido)pyridinium chloride | m.p. 151-5° C. |
| 1-(2-phenylacetamido)-4-methylpyridinium chloride | m.p. 144-7° C. |
| 1-(2-(p-chlorophenyl)acetamido)pyridinium chloride | m.p. 217-8° C. |
| 1-(2-(p-chlorophenyl)acetamido)-4-methylpyridinium chloride | m.p. 191-3° C. |
| 1-cinnamamidopyridinium chloride | m.p. 215-7° C. |
| 1-cinnamamido-4-methylpyridinium chloride | m.p. 235-9° C. |
| 1-(p-chlorocinnamamido)pyridinium chloride | m.p. 258-260° C. |
| 1-(p-chlorocinnamamido)-2-methylpyridinium chloride | m.p. 225-8° C. |
| 1-(p-chlorocinnamamido)-4-methylpyridinium chloride | m.p. 197-9° C. |
| 1-(2-(p-chlorophenoxy)acetamido)pyridinium chloride | m.p. 200-4° C. |
| 1-(2-(p-chlorophenoxy)acetamido)-4-methylpyridinium chloride | m.p. 181-2° C. |
| 1-(2-(4-chloro-o-tolyloxy)acetamido)pyridinium chloride | m.p. 180-2° C. |
| 1-(propoxycabonylamino)pyridinium chloride | m.p. 144-6° C. |
| 1-(butoxycarbonylamino)pyridinium chloride | m.p. 129-133° C. |
| 1(-isobutoxycarbonylamino)pyridinium chloride | m.p. 157-160° C. |
| 1-(pentyloxycarbonylamino)pyridinium chloride | m.p. 150-2° C. |
| 1-(octyloxycarbonylamino)pyridinium chloride | m.p. 139-141° C. |
| 1-(phenoxycarbonylamino)pyridinium chloride | m.p. 132-8° C. |
| 1-(o-chlorophenoxycarbonylamino)pyridinium chloride | m.p. 146-8° C. |
| 1-(p-chlorophenoxycarbonylamino)pyridinium chloride | m.p. 155-165° C. |
| 1-(p-tolyloxycarbonylamino)pyridinium chloride | m.p. 210° C. |
| 1-(4-chloro-m-tolyloxycarbonylamino)pyridinium chloride | m.p. 116-120° C/ |
| 1-(2,4,6-trichlorophenoxycarbonylamino)pyridinium chloride | m.p. 200° C. |
| 1-(4-benzofuranyloxycarbonylamino)pyridinium chloride | m.p. 117-127° C. |
| 1-(3-methylureido)pyridinium chloride | m.p. 155-160° C. |
| 1-(3-phenylureido)pyridinium chloride | m.p. 180-1° C. |
| 1-(3-(p-chlorophenyl)ureido)pyridinium chloride | m.p. 205° C. |
| 1-(3-(m-tolyl)ureido)pyridinium chloride | m.p. 165-7° C. |
| 1-(3-(m-methoxyphenyl)ureido)pyridinium chloride | m.p. 182-4° C. |
| 1-(3-m-chlorophenyl)ureido)pyridinium chloride | m.p. 125-9° C. |
| 1-(3-(2,5-dimethoxyphenyl)ureido)pyridinium chloride | m.p. 177-9° C. |
| 1-(3-(3-chloro-p-tolyl)ureido)pyridinium chloride | m.p. 176-8° C. |
| 1-(3-(4-chloro-o-tolyl)ureido)pyridinium chloride | m.p. 192-4° C. |
| 1-(3-(3,4-dichlorophenyl)ureido)pyridinium chloride | m.p. 188-190° C. |

| | |
|---|---|
| -continued | |
| 1-(3,3-dimethylureido)pyridinium chloride | m.p. 140° C |

EXAMPLE 96

A solution of 1-(p-chlorobenzamido)pyridinium chloride (46 parts) in water (500 parts) was treated with normal caustic soda solution (173 parts by volume). The solid product was filtered off and recrystallised from benzene to give 1-(p-chlorobenzamido)pyridinium internal salt (26 parts, 65% yield), melting point 180° C.

Analysis: Found: C, 61.65; H, 3.80; N, 12.30%. $C_{12}H_9ClN_2O$ requires: C, 61.94; H, 3.90; N, 12.04%.

EXAMPLES 97–175

The following were prepared by analogous methods to that of Example 96:

| | |
|---|---|
| 1-(p-Fluorobenzamido)pyridinium internal salt | m.p. 202° C. |
| 1-(p-Toluamido)pyridinium internal salt | m.p. 162° C. |
| 1-(2,4-Dichlorobenzamido)pyridinium internal salt | m.p. 140° C. |
| 1-(p-Nitrobenzamido)pyridinium internal salt | m.p. 253° C. |
| 1-(m-Nitrobenzamido)pyridinium internal salt | m.p. 155° C. |
| 1-(3,4-dichlorobenzamido)pyridinium internal salt | m.p. 178° C. |
| 1-(p-anisamido)pyridinium internal salt | m.p. 145° C. |
| 1-(p-chlorobenzamido)-2-methylpyridinium internal salt | m.p. 123° C. |
| 1-(o-chlorobenzamido)pyridinium internal salt | m.p. 100° C. |
| 1-(o-iodobenzamido)pyridinium internal salt | m.p. 129° C. |
| 1-(3,4-dichlorobenzamido)-2-methylpyridinium internal salt | m.p. 169° C. |
| 1-(p-toluamido)-2-methylpyridinium internal salt | m.p. 125° C. |
| 1-(o-toluamido)pyridinium internal salt | m.p. 112–4° C. |
| 1-(o-toluamido)-4-methylpyridinium internal salt | m.p. 123–5° C. |
| 1-(p-tert-butylbenzamido)-4-methylpyridinium internal salt | m.p. 200–2° C. |
| 1-(o-chlorobenzamido)-2-methylpyridinium internal salt | m.p. 141° C. |
| 1-(m-chlorobenzamido)pyridinium internal salt | m.p. 121–3° C. |
| 1-(m-chlorobenzamido)-2-methylpyridinium internal salt | m.p. 70–74° C. |
| 1-(m-chlorobenzamido)-3-methylpyridinium internal salt | m.p. 112–5° C. |
| 1-(m-chlorobenzamido)-4-methylpyridinium internal salt | m.p. 169–171° C. |
| 1-(p-chlorobenzamido)-3-methylpyridinium internal salt | m.p. 149–152° C. |
| 1-(p-chlorobenzamido)-4-methylpyridinium internal salt | m.p. 160° C. |
| 1-(p-chlorobenzamido)-2-ethylpyridinium internal salt | liquid |
| 1-(p-chlorobenzamido)-3,5-dimethylpyridinium internal salt | m.p. 50–52° C. |
| 1-(p-chlorobenzamido)-2,6-dimethylpyridinium internal salt | m.p. 90–94° C. |
| 1-(p-chlorobenzamido)-5-ethyl-2-methylpyridinium internal salt | m.p. 65–68° C. |
| 1-(p-bromobenzamido)pyridinium internal salt | m.p. 186–8° C. |
| 1-(m-anisamido)-4-methylpyridinium internal salt | m.p. 95–100° C. |
| 1-(3,4-dimethylbenzamido)pyridinium internal salt | m.p. 150–4° C. |
| 1-(3,4-dichlorobenzamido)-2-methylpyridinium internal salt | m.p. 169° C. |
| 1-(3,4-dichlorobenzamido)-2,6-dimethylpyridinium internal salt | m.p. 120–3° C. |
| 1-(3-chloro-p-toluamido)pyridinium internal salt | m.p. 159–160° C. |
| 1-(3-chloro-p-toluamido)-2-methylpyridinium internal salt | m.p. 128–130° C. |
| 1-(3-chloro-p-toluamido)-4-methylpyridinium internal salt | m.p. 194–6° C. |
| 1-(4-chloro-m-toluamido)pyridinium internal salt | m.p. 149–150° C. |
| 1-(4-chloro-m-toluamido)-2-methylpyridinium internal salt | m.p. 105–6° C. |
| 1-(4-chloro-m-toluamido)-4-methylpyridinium internal salt | m.p. 158–160° C. |
| 1-(4-nitro-m-toluamido)pyridinium internal salt | m.p. 154–6° C. |
| 1-(4-nitro-m-toluamido)-3-methylpyridinium internal salt | m.p. 163–4° C. |
| 1-(4-chloro-3-nitrobenzamido)-3-methylpyridinium internal salt | m.p. 156–8° C. |
| 1-(o-acetamidobenzamido)pyridinium internal salt | m.p. 155–160° C. |
| 1-(cyclohexylcarboxamido)pyridinium internal salt | m.p. 129–130° C. |
| 1-(cyclohexylcarboxamido)-3,5-dimethylpyridinium internal salt | m.p. 141–3° C. |
| 1-(1-naphthamido)pyridinium internal salt | m.p. 150–2° C. |
| 1-(2-naphthamido)pyridinium internal salt | m.p. 148–150° C. |
| 1-(2-furamido)pyridinium internal salt | m.p. 224–7° C. |
| 1-(2-thenamido)pyridinium internal salt | m.p. 210–2° C. |
| 1-picolinamido-3-methylpyridinium internal salt | m.p. 181–3° C. |
| 1-picolinamido-3-methylpyridinium internal salt, hydrochloride | m.p. 180–5° C. |
| 1-picolinamido-4-methylpyridinium internal salt | m.p. 208–210° C. |
| 1-(p-toluenesulphonamido)pyridinium internal salt | m.p. 214–6° C. |
| 1-(2,4,5-trichlorobenzenesulphonamido)pyridinium internal salt | m.p. 264–5° C. |
| 1-(4-chloro-3-nitrobenzenesulphonamido)pyridinium internal salt | m.p. 195–200° C. |
| 1-(2-phenylacetamido)pyridinium internal salt | m.p. 70–74° C. |
| 1-(2-phenylacetamido)-4-methylpyridinium internal salt | m.p. 96–97° C. |
| 1-(2-(p-chlorophenyl)acetamido)-4-methylpyridinium internal salt | m.p. 129–130° C. |
| 1-cinnamamidopyridinium internal salt | m.p. 160–2° C. |
| 1-(p-chlorocinnamamido)pyridinium internal salt | m.p. 125° C. |
| 1-(p-chlorocinnamamido)-2-methylpyridinium internal salt | m.p. 136–141° C. |
| 1-(p-chlorocinnamamido)-4-methylpyridinium internal salt | m.p. 216–7° C. |
| 1-(2-(4-chlorophenoxy)acetamido)-4-methylpyridinium internal salt | m.p. 135–6° C. |
| 1-(propoxycarbonylamino)pyridinium internal salt | liquid |
| 1-(butoxycarbonylamino)pyridinium internal salt | m.p. 47–49° C. |
| 1-(isobutoxycarbonylamino)pyridinium internal salt | m.p. 41–43° C. |
| 1-(pentyloxycarbonylamino)pyridinium internal salt | liquid |
| 1-(octyloxycarbonylamino)pyridinium internal salt | m.p. 39–40° C. |
| 1-(phenoxycarbonylamino)pyridinium internal salt | m.p. 116–9° C. |
| 1-(p-chlorophenoxycarbonylamino)pyridinium internal salt | m.p. 142–3° C. |

-continued

| | |
|---|---|
| 1-(4-chloro-m-tolyloxycarbonylamino)pyridinium internal salt | m.p. 150–3° C. |
| 1-(4-benzofuranyloxycarbonylamino)pyridinium internal salt | m.p. 126–7° C. |
| 1-(3-methylureido)pyridinium internal salt | m.p. 199° C. |
| 1-(3,3-dimethylureido)pyridinium internal salt | m.p. 155–7° C. |
| 1-(3-phenylureido)pyridinium internal salt | m.p. 220–2° C. |
| 1-(3-(p-chlorophenyl)ureido)pyridinium internal salt | m.p. 225–6° C. |
| 1-(3-(m-tolyl)ureido)pyridinium internal salt | m.p. 227–8° C. |
| 1-(3-(m-methoxyphenyl)ureido)pyridinium internal salt | m.p. 203–5° C. |
| 1-(3-(4-chloro-o-tolyl)ureido)pyridinium internal salt | m.p. 139–142° C. |
| 1-(3-(3,4-dichlorophenyl)ureido)pyridinium internal salt | m.p. 228–231° C. |
| 1-(3-(3-chloro-p-tolyl)ureido)pyridinium internal salt | m.p. 216–8° C. |

EXAMPLES 176–204

Aqueous solutions containing 1000, 300, 100 and 30 parts per million of the compounds listed below together with 500 ppm of a nonylphenol/ethylene oxide condensate as wetting agent were applied to 25 mm diameter leaf discs cut from French beans, *Phaseolus vulgaris*, infested with 50 to 100 one day old summer eggs of the greenhouse red spider mite, *Tetranychus telarius*. The leaf discs were then kept for 7 days at 25° C. on moist filter paper and the eggs examined. The proportion hatching out, by comparison with control leaf discs treated with water and wetting agent alone is tabulated below.

phenyl)-2,2,2-trichloroethanol), Dimethoate (O,O-dimethyl S-(N-methylcarbamoylmethyl)phosphorodithioate) and Phenkapton (S-(2,5-dichlorophenylthiomethyl)O,O-diethyl phosphorodithioate). None of these acaricides was active at 100 ppm, but 1-(p-chlorobenzamido)-pyridinium chloride prevented egg hatching at 30 ppm.

EXAMPLES 206–263

Aqueous solutions or suspensions containing 1000, 300, 100 and 30 ppm of the compounds listed in the table below were sprayed on to the foliage of French bean plants, *Phaseolus vulgaris*. When the plants were dry, they were infested with adult female greenhouse red

| Compound | 1000 ppm | 300 ppm | 100 ppm | 30 ppm |
|---|---|---|---|---|
| 1-(p-chlorobenzamido)pyridinium chloride | 0 | 0 | 0 | 0 |
| 1-(p-toluamido)pyridinium chloride | 0 | 0 | 0 | 30 |
| 1-(2,4-dichlorobenzamido)pyridinium chloride | 0 | 0 | 0 | 60 |
| 1-(m-nitrobenzamido)pyridinium chloride | 0 | 0 | | |
| 1-(p-chlorobenzamido)pyridinium internal salt | 0 | 0 | 0 | 0 |
| 1-(p-fluorobenzamido)pyridinium internal salt | 0 | 0 | | |
| 1-(p-toluamido)pyridinium internal salt | 0 | 0 | | |
| 1-(2,4-dichlorobenzamido)pyridinium internal salt | 0 | 0 | | |
| 1-(p-toluamido)-4-methylpyridinium chloride | 0 | 0 | 50 | 80 |
| 1-(p-chlorobenzamido)-2-methylpyridinium chloride | 0 | 40 | 70 | |
| 1-(p-chlorobenzamido)-4-methylpyridinium chloride | 0 | 0 | 0 | 0 |
| 1-(p-bromobenzamido)pyridinium chloride | 0 | 0 | 0 | 0 |
| 1-(p-bromobenzamido)pyridinium internal salt | 0 | 0 | 0 | 40 |
| 1-(p-iodobenzamido)pyridinium chloride | 0 | 0 | 60 | |
| 1-(2,4-dichlorobenzamido)pyridinium chloride | 0 | 0 | 70 | |
| 1-(3,4-dichlorobenzamido)pyridinium chloride | 0 | 0 | 0 | 0 |
| 1-(3,4-dichlorobenzamido)-2-methylpyridinium chloride | 0 | 0 | 0 | 10 |
| 1-(3,4-dichlorobenzamido)pyridinium internal salt | 0 | 0 | 60 | |
| 1-(3,4-dichlorobenzamido)-2-methylpyridinium internal salt | 0 | 10 | 70 | |
| 1-(4-chloro-m-toluamido)pyridinium chloride | 0 | 0 | 30 | 60 |
| 1-(4-chloro-m-toluamido)pyridinium internal salt | 0 | 0 | 0 | 0 |
| 1-cinnamamidopyridinium internal salt | 0 | 30 | 70 | |
| 1-(p-chlorocinnamamido)pyridinium chloride | 0 | 30 | 60 | |
| 1-(p-chlorocinnamamido)pyridinium internal salt | 0 | 40 | 80 | |
| 1-(3,3-dimethylureido)pyridinium chloride | 10 | 70 | 90 | |
| 1-(p-chlorophenoxycarbonylamino)pyridinium chloride | 0 | 10 | 60 | |
| 1-(p-chlorophenoxycarbonylamino)pyridinium internal salt | 0 | 20 | 70 | |
| 1-(4-chloro-m-tolyloxycarbonylamino)pyridinium chloride | 0 | 0 | 40 | 70 |
| 1-(4-chloro-m-tolyloxycarbonylamino)pyridinium internal salt | 0 | 0 | 0 | 60 |

EXAMPLE 205

A similar experiment was performed to that described in Examples 176–204 with a strain of the hop red spider mite, *Tetranchus urticae*, which was resistant to the common acaricides, for example Chlorobenzilate (ethyl 4,4'-dichlorobenzilate), Chloropropylate (isopropyl 4,4'-dichlorobenzilate), Dicofol (1,1-bis(p-chlorospider mites, *Tetranychus telarius*. After the mites had fed for two hours on the treated foliage they were removed and placed on fresh untreated leaves. The sterilant effect of the compounds was assessed by noting the percentage of eggs laid by the mites during the next 48 hours which hatched out. The results are tabulated below.

| Compound | 1000 ppm | 300 ppm | 100 ppm | 30 ppm |
|---|---|---|---|---|
| 1-(p-chlorobenzamido)pyridinium chloride | 0 | 0 | 0 | 0 |
| 1-benzamido-2-methylpyridinium chloride | 0 | 0 | 60 | |
| 1-(p-toluamido)pyridinium chloride | 0 | 0 | 0 | 60 |
| 1-(p-toluamido)pyridinium internal salt | 0 | 0 | 0 | 50 |
| 1-(p-fluorobenzamido)pyridinium chloride | 0 | 0 | 0 | 50 |
| 1-(p-fluorobenzamido)pyridinium internal salt | 0 | 0 | 0 | 60 |
| 1-(o-chlorobenzamido)-2-methylpyridinium chloride | 0 | 0 | 50 | 80 |
| 1-(m-chlorobenzamido)pyridinium chloride | 0 | 0 | 0 | 10 |
| 1-(m-chlorobenzamido)pyridinium internal salt | 0 | 0 | 0 | 50 |
| 1-(m-chlorobenzamido)-2-methylpyridinium chloride | 0 | 40 | 70 | |
| 1-(m-chlorobenzamido)-2-methylpyridinium internal salt | 0 | 40 | 80 | |
| 1-(p-chlorobenzamido)-2-methylpyridinium chloride | 0 | 0 | 0 | 0 |
| 1-(p-chlorobenzamido)-3-methylpyridinium chloride | 0 | 0 | 0 | 0 |
| 1-(p-chlorobenzamido)-4-methylpyridinium chloride | 0 | 0 | 0 | 0 |
| 1-(p-chlorobenzamido)-2-ethylpyridinium chloride | 0 | 50 | 90 | |
| 1-(p-chlorobenzamido)pyridinium internal salt | 0 | 0 | 0 | 0 |
| 1-(p-chlorobenzamido)-2-methylpyridinium internal salt | 0 | 0 | 0 | 0 |
| 1-(p-chlorobenzamido)-3-methylpyridinium internal salt | 0 | 0 | 0 | 0 |
| 1-(p-chlorobenzamido)-4-methylpyridinium internal salt | 0 | 0 | 0 | 0 |
| 1-(p-chlorobenzamido)-2-ethylpyridinium internal salt | 0 | 0 | 60 | |
| 1-(p-chlorobenzamido)-3,5-dimethylpyridinium internal salt | 0 | 0 | 0 | 50 |
| 1-(p-bromobenzamido)pyridinium chloride | 0 | 0 | 0 | 0 |
| 1-(p-bromobenzamido)pyridinium internal salt | 0 | 0 | 0 | 0 |
| 1-(p-iodobenzamido)pyridinium chloride | 0 | 0 | 0 | 0 |
| 1-(p-anisamido)pyridinium chloride | 0 | 60 | | |
| 1-(p-anisamido)pyridinium internal salt | 0 | 60 | | |
| 1-(2,4-dichlorobenzamido)pyridinium chloride | 0 | 10 | 60 | |
| 1-(3,4-dichlorobenzamido)pyridinium chloride | 0 | 0 | 0 | 0 |
| 1-(3,4-dichlorobenzamido)-2-methylpyridinium chloride | 0 | 0 | 0 | 50 |
| 1-(3,4-dichlorobenzamido)pyridinium internal salt | 0 | 0 | 10 | 50 |
| 1-(3,4-dichlorobenzamido)-2-methylpyridinium internal salt | 0 | 0 | 50 | 90 |
| 1-(3,4-dichloro-N-methylbenzamido)pyridinium methyl sulphate | 0 | 0 | 0 | 0 |
| 1-(m-nitrobenzamido)pyridinium chloride | 0 | 10 | 60 | |
| 1-(p-nitrobenzamido)-2-methylpyridinium chloride | 0 | 0 | 10 | 60 |
| 1-(p-nitrobenzamido)pyridinium internal salt | 0 | 0 | 0 | 0 |
| 1-(bis(p-chlorobenzoyl)amino)pyridinium chloride | 0 | 0 | 0 | 0 |
| 1-(cyclohexylcaboxamido)pyridinium chloride | 0 | 10 | 60 | |
| 1-(cyclohexylcarboxamido)pyridinium internal salt | 0 | 50 | 70 | |
| 1-picolinamido-3-methylpyridinium internal salt | 40 | | | |
| 1-picolinamido-4-methylpyridinium internal salt | 50 | | | |
| 1-(2-phenylacetamido)pyridinium chloride | 40 | | | |
| 1-cinnamamidopyridinium chloride | 0 | 0 | 10 | 50 |
| 1-cinnamamidopyridinium internal salt | 0 | 0 | 20 | 60 |
| 1-(2-p-chlorophenoxy)acetamidopyridinium chloride | 10 | 60 | | |
| 1-(butoxycarbonylamino)pyridinium chloride | 0 | 0 | 20 | 60 |
| 1-(butoxycarbonylamino)pyridinium internal salt | 0 | | | |
| 1-(isobutoxycarbonylamino)pyridinium internal salt | 0 | | | |
| 1-(pentyloxycarbonylamino)pyridinium internal salt | 0 | | | |
| 1-(phenoxycarbonylamino)pyridinium chloride | 0 | 0 | 50 | |
| 1-(phenoxycarbonylamino)pyridinium internal salt | 0 | 0 | 10 | 60 |
| 1-(p-chlorophenoxycarbonylamino)pyridinium chloride | 0 | 0 | 0 | 0 |
| 1-(p-chlorophenoxycarbonylamino)pyridinium internal salt | 0 | 0 | 0 | 0 |
| 1-(p-tolyloxycarbonylamino)pyridinium chloride | 0 | 0 | 0 | |
| 1-(4-chloro-m-tolyloxycarbonylamino)pyridinium chloride | 0 | 0 | 0 | |
| 1-(4-chloro-m-tolyloxycarbonylamino)pyridinium internal salt | 0 | 0 | 0 | |
| 1-(4-benzofuranyloxycarbonylamino)pyridinium chloride | 0 | 0 | 60 | |
| 1-(4-benzofuranyloxycarbonylamino)pyridinium internal salt | 0 | 20 | 80 | |
| 1-(3-(p-chlorophenyl)ureido)pyridinium chloride | 0 | 0 | 20 | 70 |

EXAMPLE 264

French bean plants, *Phaseolus vulgaris*, were grown in 75 mm diameter pots and the soil watered with 10 ml of a 1000 ppm aqueous solution of 1-(p-chlorobenzamido)-pyridinium chloride. After 24 hours the plants were infested with adult female red spider mites, *Tetranychus telarius*, which were allowed to feed on the foliage for 24 hours and then removed to untreated plants. None of the eggs which they laid during the next 48 hours hatched out, demonstrating the systemic activity of the compound.

EXAMPLE 265

Aqueous solutions containing 1000 and 300 parts per million of 1-(p-chlorobenzamido)-2-methylpyridinium chloride were sprayed on to young french bean plants, *Phaseolus vulgaris* which had previously been infested with 50 adult greenhouse red spider mites *Tetranychus telarius*. The treated plants were then kept at 25° C. for 48 hours, after which time all the mites were found to be dead.

EXAMPLE 266

1-(3,4-dichlorobenzamido)pyridinium internal salt (20 parts) and dimethyl sulphate (100 parts) were heated together at 100° C. for four hours. On cooling, crystals separated which were filtered off, washed and dried to give 1-(3,4-dichloro-N-methylbenzamido)pyridinium methyl sulphate (15 parts), melting point 135° C.

EXAMPLE 267

A solution of 1-(p-chlorobenzamido)pyridinium internal salt (20 parts) in p-chlorobenzoyl chloride was allowed to stand for two hours at 25° C. The crystalline solid which formed was filtered off, washed and dried to give 1-(bis(p-chlorobenzoyl)amino)pyridinium chloride (20 parts), melting point 195° C.

Analysis: Found: C, 55.65; H, 3.25; N, 6.75%. $C_{19}H_{13}Cl_3N_2O_2$ requires: C, 55.97; H, 3.21; N, 6.87%.

EXAMPLE 268

A suitable wettable powder formulation was prepared by admixing:

| | |
|---|---|
| 1-(p-chlorobenzamido)pyridinium internal salt | 25% by weight |
| Wetting agent | 3% by weight |
| Dyapol PFS (sodium salt of sulphonated cresol/formaldehyde condensate), defloculating agent | 3% by weight |
| China clay | 69% by weight |

What is claimed is:

1. A compound of the general formula

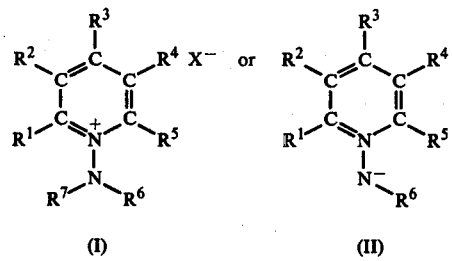

in which
$R^1$, $R^2$, $R^3$, $R^4$ and $R^5$ are the same or different and each represents hydrogen or alkyl of 1 to 4 carbon atoms;
$R^6$ represents a group of formula $COR^{10}$ in which $R^{10}$ represents styryl substituted by halogen;
$R^7$ represents hydrogen, alkyl of 1 to 4 carbon atoms or benzoyl substituted by halogen; and
$X^-$ represents one equivalent of an anion.

2. A compound according to claim 1, wherein $R^7$ represents hydrogen.

3. A compound according to claim 1, wherein at least three of $R^1$, $R^2$, $R^3$, $R^4$ and $R^5$ represents hydrogen.

4. A compound according to claim 1, wherein at least four of $R^1$, $R^2$, $R^3$, $R^4$ and $R^5$ represents hydrogen.

5. A compound according to claim 1, wherein at least one of $R^1$ and $R^5$ represents hydrogen.

6. A compound according to claim 1, wherein $R^{10}$ is chlorostyryl.

* * * * *